US00PP19574P2

(12) United States Plant Patent
Wijnhout

(10) Patent No.: US PP19,574 P2
(45) Date of Patent: Dec. 16, 2008

(54) ***HEUCHERA* PLANT NAMED 'PWHEU0109'**

(50) Latin Name: *Heuchera hybrida*
Varietal Denomination: PWHEU0109

(76) Inventor: Aad Wijnhout, Muntstraat 26, 2165 VJ Lisserbroek (NL)

( * ) Notice: Subject to any disclaimer, the term of this patent is extended or adjusted under 35 U.S.C. 154(b) by 0 days.

(21) Appl. No.: 11/800,774

(22) Filed: May 7, 2007

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Annette H Para
(74) *Attorney, Agent, or Firm*—C. A. Whealy

(57) ABSTRACT

A new and distinct cultivar of *Heuchera* plant named 'PWHEU0109', characterized by its compact and mounded growth habit; vigorous growth habit; freely branching habit; and large purple and silver-colored leaves.

1 Drawing Sheet

Botanical designation: *Heuchera hybrida.*
Cultivar denomination: 'PWHEU0109'.

BACKGROUND OF THE INVENTION

The present invention relates to a new and distinct cultivar of *Heuchera,* botanically known as *Heuchera hybrida* and hereinafter referred to by the name 'PWHEU0109'.

The new *Heuchera* is a product of a planned breeding program conducted by the Inventor in Lisse, The Netherlands. The objective of the breeding program is to create new Heuchera cultivars with attractive leaf coloration.

The new *Heuchera* originated from a cross-pollination in Lisse, The Netherlands of two unnamed selections of *Heuchera hybrida,* not patented. The new *Heuchera* was discovered and selected by the Inventor as a single flowering plant within the progeny of the stated cross-pollination in a controlled environment in Lisse, The Netherlands in October, 2001.

Asexual reproduction of the new *Heuchera* by tissue culture in a controlled environment in Gensingen, Germany since November, 2001, has shown that the unique features of this new *Heuchera* are stable and reproduced true to type in successive generations.

SUMMARY OF THE INVENTION

The cultivar PWHEU 0109 has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'PWHEU0109'. These characteristics in combination distinguish 'PWHEU0109' as a new and distinct cultivar of *Heuchera:*

1. Compact and mounded growth habit.
2. Vigorous growth habit.
3. Freely branching habit.
4. Large purple and silver-colored leaves.

Plants of the new *Heuchera* differ from plants of the parent selections primarily in leaf coloration.

Plants of the new *Heuchera* can be compared to plants of the Coleus cultivar Amethyst Myst, not patented. In side-by-side comparisons conducted by the Inventor in Lisse, The Netherlands, plants of the new *Heuchera* differed from plants of the cultivar Amethyst Myst in the following characteristics:

1. Plants of the new *Heuchera* were more freely branching than plants of the cultivar Amethyst Myst.
2. Plants of the new *Heuchera* had shorter leaf petioles than plants of the cultivar Amethyst Myst.
3. Plants of the new *Heuchera* and the cultivar Amethyst-Myst differed in leaf color as plants.

BRIEF DESCRIPTION OF THE PHOTOGRAPHS

The accompanying colored photographs illustrate the overall appearance of the new *Heuchera,* showing the colors as true as it is reasonably possible to obtain in colored reproductions of this type. Colors in the photographs may differ slightly from the color values cited in the detailed botanical description which accurately describe the colors of the new *Heuchera.*

The photograph at the bottom of the sheet comprises a side perspective view of a typical plant of 'PWHEU0109' grown in a container.

The photograph at the top of the sheet is a close-up view of typical leaves of 'PWHEU0109'.

DETAILED BOTANICAL DESCRIPTION

The aforementioned photographs and following observations, measurements and values describe plants grown in Bonsall, Calif. in containers in a shaded polyethylene-covered greenhouse during the winter and under conditions which closely approximate commercial production. During the production of the plants, day temperatures ranged from about 16° C. to 24° C. and night temperatures ranged from about 12° C. to 16° C. Plants were about three months old when the photographs and the description were taken. In the description, color references are made to The Royal Horticultural Society Colour Chart, 1995 Edition, except where general terms of ordinary dictionary significance are used.

Botanical classification: *Heuchera hybrida* cultivar PWHEU0109.

Parentage:

*Female, or seed, parent.*—Unnamed selection of *Heuchera hybrida,* not patented.

*Male, or pollen, parent.*—Unnamed selection of *Heuchera hybrida,* not patented.

Propagation:

*Type.*—By tissue culture.

*Time to produce a rooted young plant.*—About seven weeks at 26° C.

*Root description.*—Fine, fibrous; white to ivory in color.

*Rooting habit.*—Moderate branching; moderately dense.

Plant description:

*Plant and growth habit.*—Compact and mounded growth habit. Vigorous growth habit. Freely branching; about six to eight lateral branches develop per plant.

*Plant height.*—About 8.5 cm.

*Plant diameter.*—About 24 cm.

Lateral branch description:

*Length.*—About 1.7 cm.

*Diameter.*—About 1 cm.

*Internode length.*—About 3 mm.

*Strength.*—Strong.

*Texture.*—Smooth, glabrous.

*Color.*—Close to 70A.

Foliage description:

*Arrangement.*—Alternate, simple.

*Length.*—About 9 cm.

*Width.*—About 9.2 cm.

*Shape.*—Orbicular.

*Apex.*—Rounded.

*Base.*—Cordate to auriculate.

*Margin.*—Crenate, sinuate, shallowly lobed.

*Texture, upper surface.*—Smooth, glabrous.

*Texture, lower surface.*—Pubescence along veins.

*Venation pattern.*—Palmate; reticulate.

*Color.*—Developing foliage, upper surface: 187A. Developing foliage, lower surface: More violet than 183A. Fully expanded foliage, upper surface: Ground color, 187A tinted with 197A; venation, darker than 79A. Fully expanded foliage, lower surface: 187A; venation, 187A.

*Petiole length.*—About 8.5 mm.

*Petiole diameter.*—About 2 mm.

*Petiole texture, upper and lower surfaces.*—Sparsely pubescent.

*Petiole color, upper surface.*—187A.

*Petiole color, lower surface.*—Slightly more grey than 187A.

Flower description: Plants of the new *Heuchera* do not develop flowers.

Pathogen/pest resistance: Plants of the new *Heuchera* have not been observed to be resistant to pests and pathogens common to *Heuchera.*

Garden performance: Plants of the new *Heuchera* have been observed to tolerate wind and rain and have good garden performance.

Temperature tolerance: Plants of the new *Heuchera* have been observed to tolerate temperatures from about 0° C. to about 35° C.

It is claimed:

1. A new and distinct *Heuchera* plant named 'PWHEU0109' as illustrated and described.

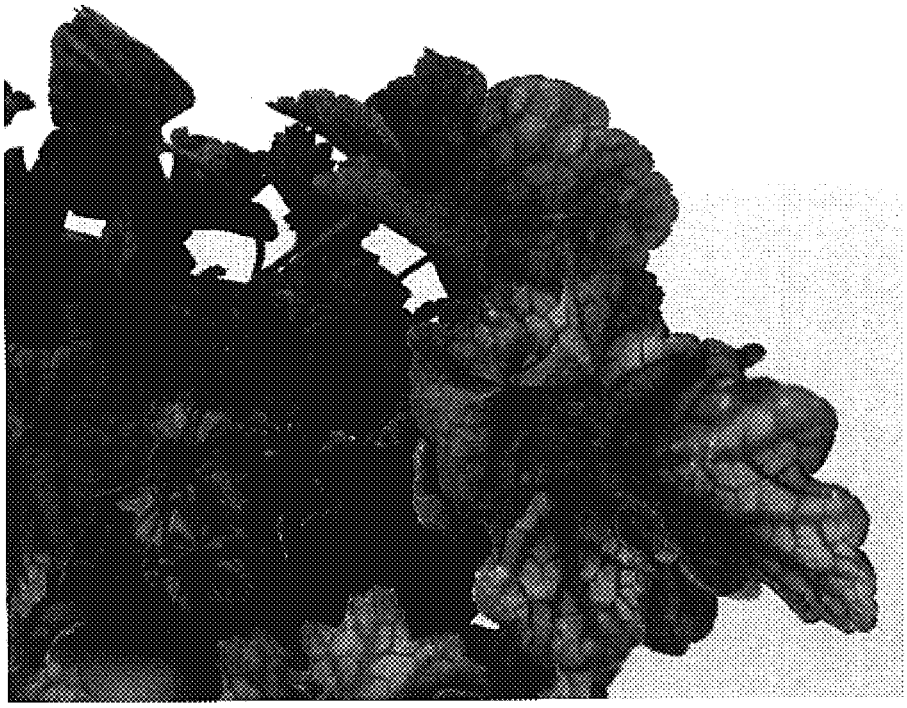
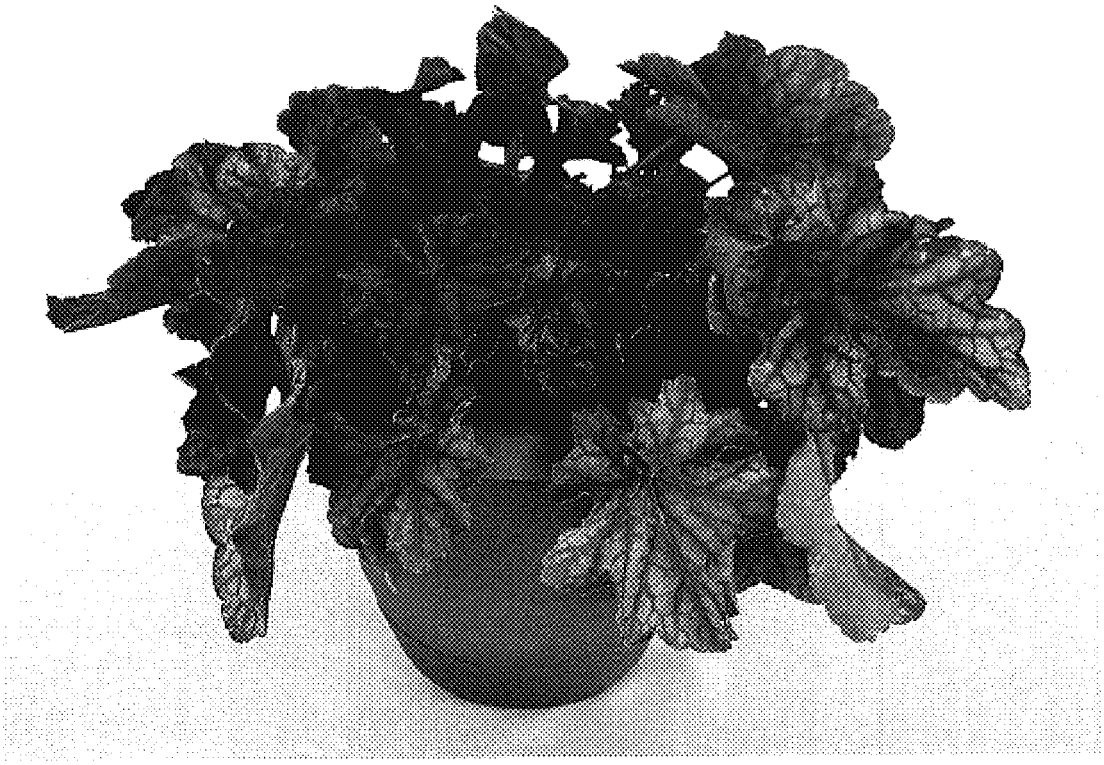

* * * * *